(12) United States Patent
Kurosaka

(10) Patent No.: US 11,602,370 B2
(45) Date of Patent: Mar. 14, 2023

(54) TREATMENT INSTRUMENT WITH VIBRATION GENERATING DEVICE

(71) Applicant: Olympus Corporation, Hachioji (JP)

(72) Inventor: Satoshi Kurosaka, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 457 days.

(21) Appl. No.: 16/744,441

(22) Filed: Jan. 16, 2020

(65) Prior Publication Data
US 2020/0146708 A1    May 14, 2020

Related U.S. Application Data

(63) Continuation of application No. PCT/JP2017/026114, filed on Jul. 19, 2017.

(51) Int. Cl.
*A61B 17/32* (2006.01)
*A61B 90/50* (2016.01)
(Continued)

(52) U.S. Cl.
CPC ........... *A61B 17/320092* (2013.01); *A61B 17/320068* (2013.01); *A61B 18/1445* (2013.01);
(Continued)

(58) Field of Classification Search
CPC .... A61B 17/320092; A61B 17/320068; A61B 90/50; A61B 18/1445;
(Continued)

(56) References Cited

U.S. PATENT DOCUMENTS 6,204,592 B1    3/2001    Hur
10,799,257 B2 *  10/2020    Worthington ........ A61B 17/072
(Continued)

FOREIGN PATENT DOCUMENTS

JP    H10-127655 A    5/1998
JP    2002-35002 A    2/2002
(Continued)

OTHER PUBLICATIONS

Oct. 10, 2017 International Search Report issued in International Patent Application No. PCT/JP2017/026114.
(Continued)

*Primary Examiner* — Erich G Herbermann
(74) *Attorney, Agent, or Firm* — Oliff PLC

(57) ABSTRACT

The disclosed technology is directed to a treatment instrument having a vibration generating device and a handle for operation. The vibration generating device comprises a housing and a generator including a transducer disposed within the housing. The transducer generates vibration by using electric energy and a first electric contact disposed on the housing. A connector is rotatable about a predetermined rotational axis with respect to the housing of the generator. A coupler is disposed in the connector and having a second electric contact rotatable about the predetermined rotational axis with respect to the first electric contact in a state in which an electric connection of the second electric contact to the first electric contact is maintained. The connector further includes a conductive member forming a part of an electric path of a current that flows based on an operating input at an operating member provided on the handle.

10 Claims, 7 Drawing Sheets

(51) Int. Cl.
*A61B 18/14* (2006.01)
*A61B 17/00* (2006.01)

(52) U.S. Cl.
CPC .... *A61B 90/50* (2016.02); *A61B 2017/00424* (2013.01); *A61B 2017/320094* (2017.08)

(58) Field of Classification Search
CPC ......... A61B 2017/320094; A61B 2017/00424; A61B 1/0053; A61B 2017/0046; A61B 2017/292; A61B 17/2841; A61B 17/2909
See application file for complete search history.

(56) References Cited

U.S. PATENT DOCUMENTS

| | | | |
|---|---|---|---|
| 2002/0107538 A1 | 8/2002 | Shibata et al. | |
| 2012/0116261 A1 | 5/2012 | Mumaw et al. | |
| 2013/0090675 A1 | 4/2013 | Mumaw et al. | |
| 2015/0051516 A1* | 2/2015 | Sanai | A61B 17/320092 601/2 |
| 2015/0335347 A1 | 11/2015 | Hirai et al. | |
| 2017/0207467 A1* | 7/2017 | Shelton, IV | H01M 10/48 |
| 2018/0296238 A1 | 10/2018 | Kanno et al. | |

FOREIGN PATENT DOCUMENTS

| | | |
|---|---|---|
| JP | 2010-162216 A | 7/2010 |
| JP | 2013-81777 A | 5/2013 |
| JP | 2013-545534 A | 12/2013 |
| WO | 2014/007168 A1 | 1/2014 |
| WO | 2017/110630 A1 | 6/2017 |

OTHER PUBLICATIONS

Jan. 21, 2020 International Preliminary Report on Patentability issued in International Patent Application No. PCT/JP2017/026114.

* cited by examiner

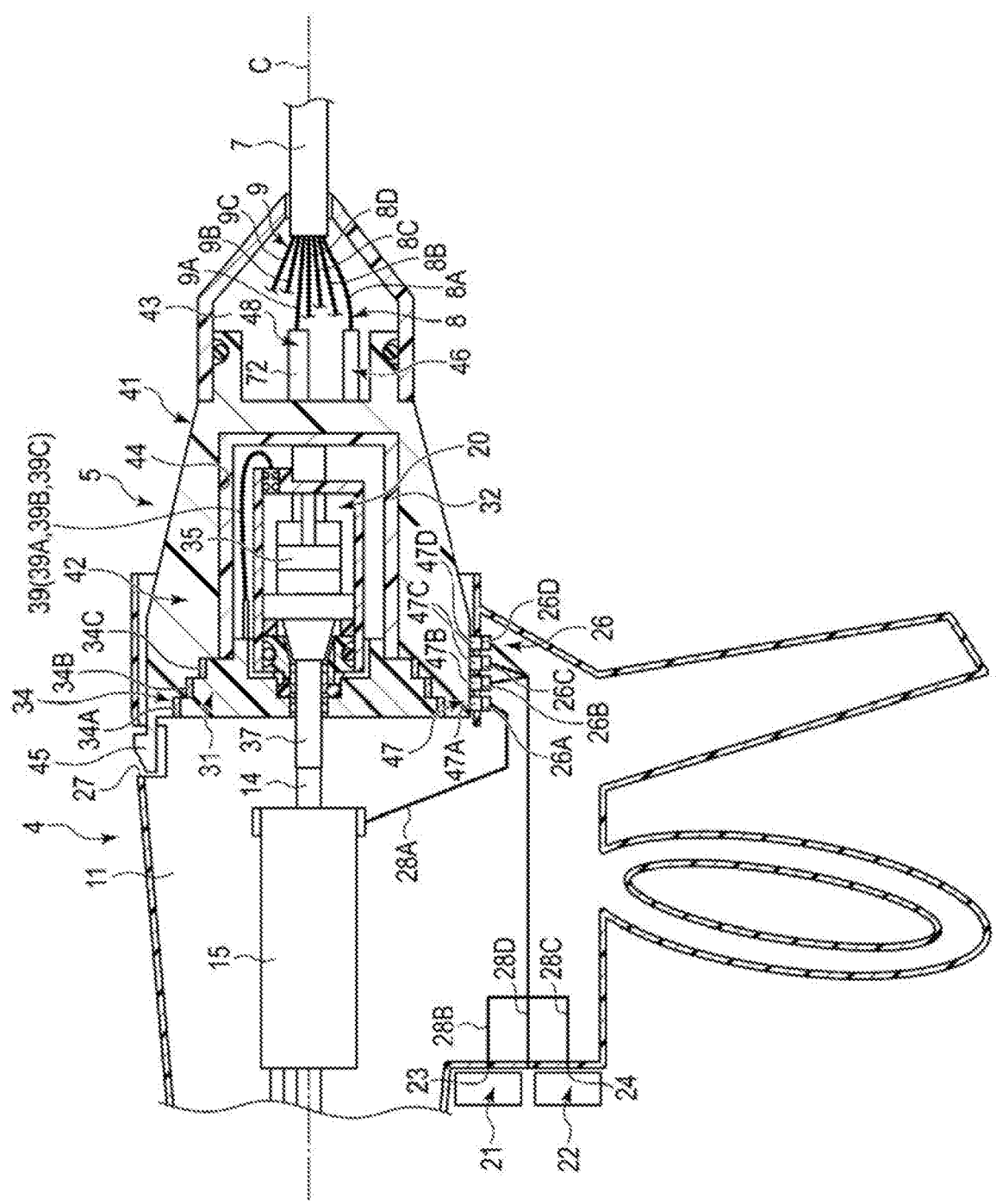
F I G. 2

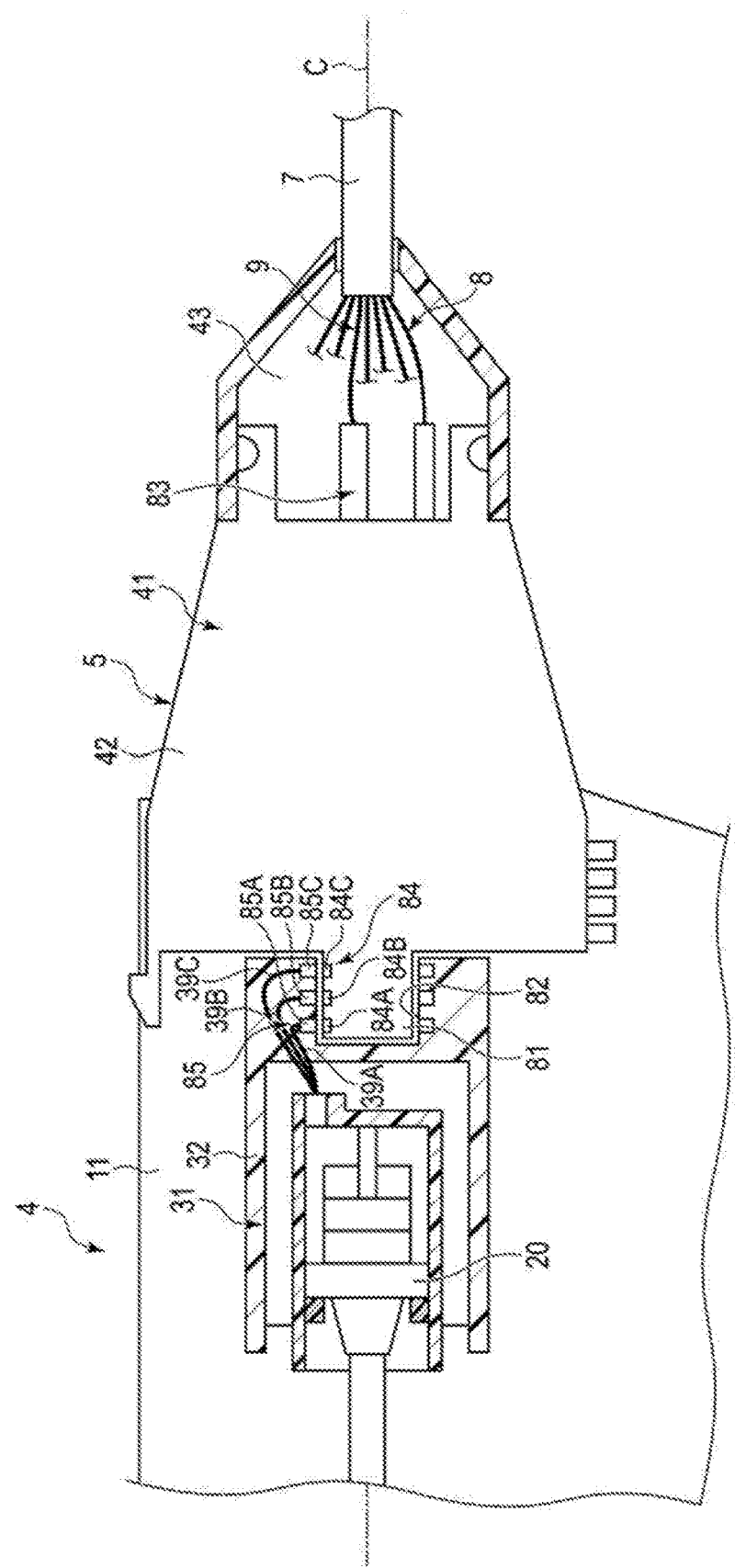

TREATMENT INSTRUMENT WITH VIBRATION GENERATING DEVICE

CROSS-REFERENCE TO RELATED APPLICATION

This application is a continuation application of PCT Application No. PCT/JP 2017/026114 filed on Jul. 19, 2017, which is hereby incorporated by reference in its entirety.

TECHNICAL FIELD

The disclosed technology relates to a vibration generating device including an ultrasonic transducer that generates an ultrasonic vibration to be transmitted to an end effector that treats a treatment target such as a biological tissue or the like. The disclosed technology also relates to a treatment instrument having the vibration generating device, a handle unit, and a treatment unit, and a treatment system including the treatment instrument and a power supply device.

DESCRIPTION OF THE RELATED ART

US Patent Application 2015/0335347A1 discloses a treatment instrument including an end effector that can hold a biological tissue such as a blood vessel or the like between a pair of holding pieces. The treatment instrument includes a vibration generating device. The vibration generating device includes an ultrasonic transducer. In addition, the treatment instrument is connected with a cable within which electric wiring for supplying electric energy to the ultrasonic transducer or the like is extended. Electric energy is supplied to the ultrasonic transducer via the electric wiring or the like extended within the cable. The ultrasonic transducer thereby generates an ultrasonic vibration. The ultrasonic vibration generated by the ultrasonic transducer is transmitted to the end effector, and is applied to the treatment target held between the pair of holding pieces.

The treatment instrument of US Patent Application 2015/0335347A1 has a rotary operating knob disposed on a treatment instrument main body or the casing. The end effector and the ultrasonic transducer are rotated together with respect to the casing by an operation at the rotary operating knob. At this time, the cable is desired not to be rotated together with the ultrasonic transducer, and the occurrence of a twist of the cable is desired to be prevented. In addition, electric connection of the wiring within the cable to the ultrasonic transducer is desired to be ensured even when the ultrasonic transducer is rotated with respect to the cable.

BRIEF SUMMARY OF EMBODIMENTS

The disclosed technology has been made in view of the problem described hereinbefore.

One aspect of the disclosed technology is directed to a treatment instrument having a vibration generating device and a handle for operation. The vibration generating device comprises a housing and a generator including a transducer disposed within the housing. The transducer generates vibration by using electric energy and a first electric contact disposed on the housing. A connector is rotatable about a predetermined rotational axis with respect to the housing of the generator. A coupler is disposed in the connector and having a second electric contact rotatable about the predetermined rotational axis with respect to the first electric contact in a state in which an electric connection of the second electric contact to the first electric contact is maintained. The connector further includes a conductive member forming a part of an electric path of a current that flows based on an operating input at an operating member provided on the handle.

Another aspect of the disclosed technology is directed to a treatment instrument comprises a handle unit having a handle for operation. A rod member is supported by the handle and transmitting vibration on a longitudinal axis. A treatment unit is disposed at a distal end of the rod member and performing treatment by applying the vibration to a biological tissue. A vibration generating device is configured to be attached to the handle unit. The vibration generating device includes a housing and a generator including a transducer disposed within the housing. The transducer generates vibration by using electric energy and a first electric contact disposed on the housing. A connector rotatable about a predetermined rotational axis with respect to the housing of the generator. A coupler is disposed in the connector and having a second electric contact rotatable about the predetermined rotational axis with respect to the first electric contact in a state in which an electric connection of the second electric contact to the first electric contact is maintained. The connector further includes a conductive member forming a part of an electric path of a current that flows based on an operating input at an operating member provided on the handle.

A further aspect of the disclosed technology is directed to a treatment system comprises a treatment instrument including a handle unit. The handle unit includes a handle for operation. A rod member is supported by the handle and transmitting vibration on a longitudinal axis. A treatment unit is disposed at a distal end of the rod member and performing treatment by applying the vibration to both a biological tissue and a vibration generating device. A cable having one end connected to the vibration generating device and a power supply device connected to an opposed end of the one end of the cable. The vibration generating device includes a housing and a generator including a transducer disposed within the housing. The transducer generates the vibration by using electric energy and a first electric contact is disposed on the housing. The connector rotatable about a predetermined rotational axis with respect to the housing of the generator. A coupler is disposed in the connector and having a second electric contact rotatable about the predetermined rotational axis with respect to the first electric contact in a state of being electrically connected to the first electric contact. The connector further includes a conductive member connected to the power supply device and the cable and forming a part of an electric path of a current that flows based on an operating input at an operating member provided on the handle.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

FIG. 2 is a diagram schematically depicting an internal configuration of a treatment instrument according to the first embodiment.

FIG. 8 is a diagram schematically depicting an internal configuration of a treatment instrument according to a second embodiment.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

It is an object of the disclosed technology to provide a vibration generating device including an ultrasonic transducer, the vibration generating device ensures electric connection between wiring within a cable and the ultrasonic transducer and prevents a twist of the cable when the ultrasonic transducer is rotated with respect to a casing and the cable, a treatment instrument including the vibration generating device, a handle unit, and a treatment unit, and a treatment system including the treatment instrument and a power supply device.

First Embodiment

Figure 1:
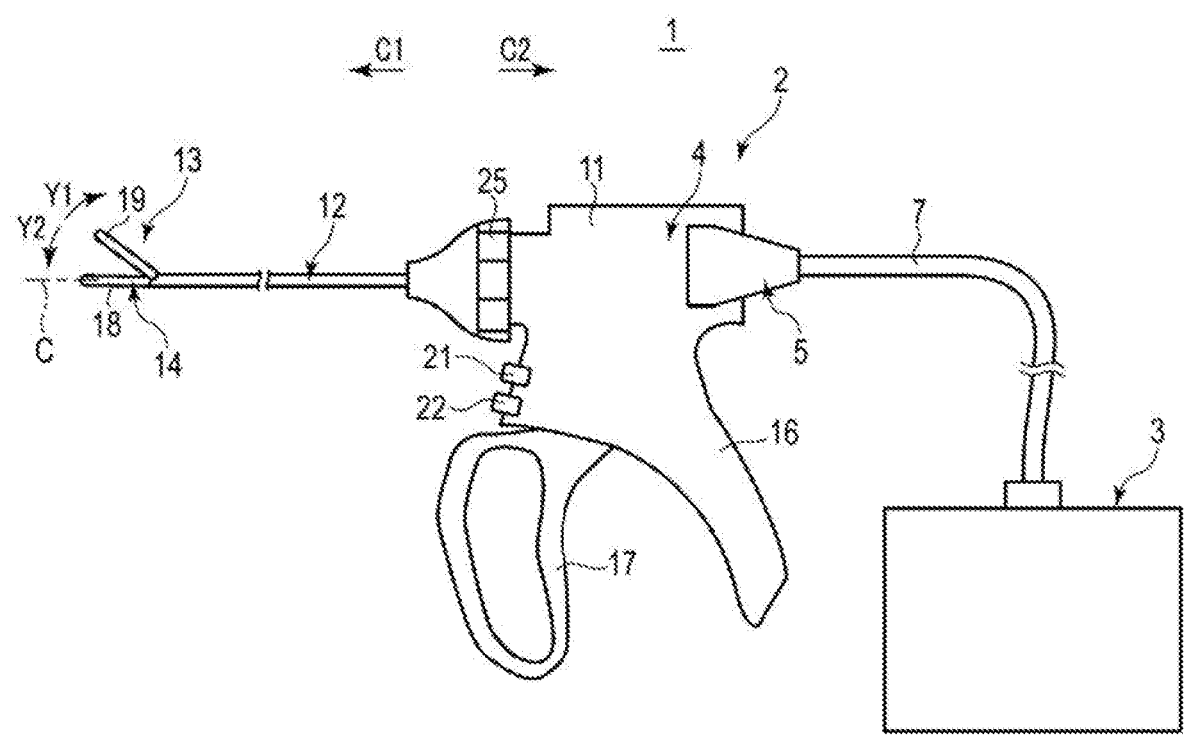
FIG. 1 is a diagram schematically depicting a treatment system according to a first embodiment.

A first embodiment of the disclosed technology will be described with reference to FIGS. 1 to 7. FIG. 1 is a diagram depicting a treatment system 1 according to the present embodiment. As depicted in FIG. 1, the treatment system 1 includes a treatment instrument 2 and a power supply device 3. The treatment instrument 2 includes a handle unit 4, i.e., a surgical device, and a vibration generating device 5 detachably attached to the handle unit 4. One end of a cable 7 is connected to the vibration generating device 5. Another end of the cable 7 is detachably connected to the power supply device 3. The handle unit 4 is discarded after the usage of the treatment instrument 2. The vibration generating device 5 is subjected to cleaning, disinfection, sterilization, and the like, and used again (reused) after the usage of the treatment instrument 2.

The handle unit 4 includes: a holdable casing 11, i.e., a handle side housing; a shaft 12, i.e., a sheath, which is coupled to a distal end side of the casing 11, i.e., a treatment instrument main body; and an end effector 13 disposed at a distal end portion of the shaft 12. The shaft 12 is extended with a longitudinal axis C as a central axis thereof. Here, a direction along the longitudinal axis C is assumed to be a longitudinal direction. In addition, one side in the longitudinal direction is assumed to be a distal end side (arrow C1 side), and another side in the longitudinal direction is assumed to be a proximal end side (arrow C2 side).

The casing 11 has a grip 16, i.e., a fixed handle. In addition, a handle 17, i.e., a movable handle, is rotatably attached to the casing 11. The handle 17 is rotatably coupled to the casing 11. The handle 17 is opened or closed with respect to the grip 16 by rotating the handle 17 with respect to the casing 11.

The end effector 13 includes a pair of holding pieces 18 and 19, i.e., a clamp member. A first holding piece 18 and a second holding piece 19 can be opened and closed relative to each other. The first holding piece 18 is supported by the shaft 12. The second holding piece 19 is rotatably attached to the distal end portion of the shaft 12.

The handle 17 and the second holding piece 19 are coupled to each other via a movable shaft 15 (see FIG. 2) extended along the longitudinal direction within the shaft 12. When the handle 17 is opened or closed with respect to the grip 16, the movable shaft 15 moves along the longitudinal direction with respect to the shaft 12 and the casing 11 to open or close the pair of holding pieces 18 and 19.

The opening and closing directions of the end effector 13 intersect the longitudinal axis C (are substantially perpendicular to the longitudinal axis C). Of the opening and closing directions of the end effector 13, a side to which the second holding piece 19 opens with respect to the first holding piece 18 is assumed to be an opening direction (arrow Y1) of the second holding piece 19, and a side to which the second holding piece 19 is closed with respect to the first holding piece 18 is assumed to be a closing direction (arrow Y2) of the second holding piece 19.

The shaft 12 is attached to the casing 11 so as to be rotatable about the longitudinal axis C. In addition, a rotary operating knob 25 is attached to a proximal end portion of the shaft 12. The shaft 12 is inserted into the rotary operating knob 25 from the distal end side, and is attached to the rotary operating knob 25. An operation of rotating the end effector 13 about the longitudinal axis C is input at the rotary operating knob 25 by rotating the rotary operating knob 25 with respect to the casing 11 about the longitudinal axis C. The rotary operating knob 25, the shaft 12, and the end effector 13 are rotated together about the longitudinal axis C with respect to the casing 11 by the operating input at the rotary operating knob 25.

Figure 3:
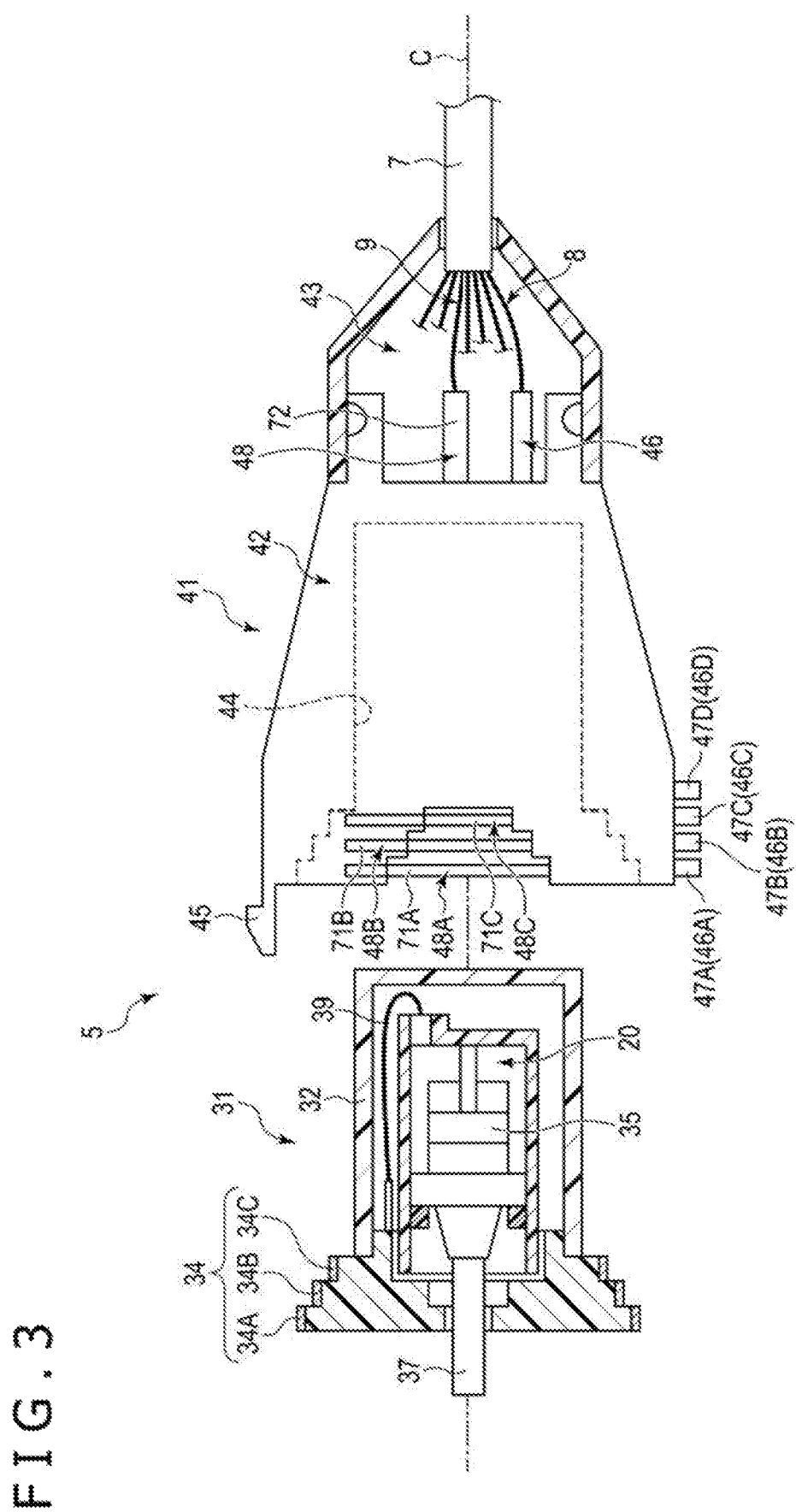
FIG. 3 is a diagram schematically depicting a state in which a generator and a coupler according to the first embodiment are detached from each other.

As depicted in FIG. 2 and FIG. 3, the vibration generating device 5 includes a generator unit 31, i.e., a generator, and a coupler 41. The generator unit 31, i.e., an ultrasonic transducer structure, is housed within the coupler 41. The generator unit 31 and the coupler 41 can be detached from each other. In addition, the generator unit 31 and the coupler 41 can rotate with respect to each other about a predetermined rotational axis, i.e., longitudinal axis C.

In a certain example, a seal member is disposed between the generator unit 31 and the coupler 41, and is formed in a state in which the generator unit 31 and the coupler 41 are slidable with respect to each other and cannot be separated from each other. Used as the seal member is, for example, a heat-resistant resin such as PTFE (polytetrafluoroethylene) or the like.

The coupler 41 includes a connector 42. The connector 42 is formed in a bell shape or socket shape having a groove portion 44 recessed toward a proximal end side. The groove portion 44 opens toward the distal end side. The generator unit 31 is housed into the coupler 41 by inserting a housing 32 of the generator unit 31 into the groove portion 44. The vibration generating device 5 including the generator unit 31 and the coupler 41 is thus formed.

The connector 42 includes a cable connecting portion 43. The cable connecting portion 43 is disposed in a proximal end portion of the connector 42. One end of the cable 7 is connected to the cable connecting portion 43. In the cable connecting portion 43, the cable 7 extends from the connector 42 to the proximal end side.

The connector 42 includes an engaging portion 45, i.e., an attachment. In addition, the casing 11 of the handle unit 4 has an engaging hole 27 engageable with the engaging portion 45. The vibration generating device 5 is attached to a proximal end portion of the casing 11 of the handle unit 4 from the proximal end side. At this time, the vibration generating device 5 is attached in a state in which the groove portion 44 of the coupler 41 faces the distal end side. The vibration generating device 5 is attached to the handle unit 4 by engaging the engaging portion 45 with the engaging hole 27. At this time, the coupler 41 is fixed to the casing 11 of the handle unit 4, so that movement of the coupler 41 with respect to the casing 11 is restricted.

In addition, in a state in which the vibration generating device 5 is attached to the handle unit 4, the generator unit 31 is housed within the treatment instrument 2, and is not exposed to the outside. In addition, a part of the external surface of the connector 42 of the coupler 41 forms a part of the external surface of a proximal end portion of the treatment instrument 2.

Within the treatment instrument 2, a rod member 14, i.e., a probe, is extended along the longitudinal axis C from the inside of the casing 11 to the distal end side. The rod member 14 is supported by the shaft 12. In addition, the rod member 14 is formed of a material having conductivity and high vibration transmissibility. The rod member 14 is, for example, formed of a titanium alloy or the like. The rod member 14 is extended from the inside of the casing 11 through the inside of the shaft 12 to the distal end side. A distal end portion of the rod member 14 projects from a distal end of the shaft 12 to the distal end side. The first holding piece 18 is formed by the projecting portion of the rod member 14 which portion projects from the shaft 12. In addition, when the rotary operating knob 25 is rotated about the longitudinal axis C with respect to the casing 11, the rod member 14 rotates about the longitudinal axis C with respect to the casing 11 together with the rotary operating knob 25 and the shaft 12.

The generator unit 31 includes the housing 32, i.e., a transducer housing, and an ultrasonic transducer 20. The housing 32 is electrically insulative. The ultrasonic transducer 20 is housed within the housing 32, and is supported by the housing 32. The ultrasonic transducer 20 generates an ultrasonic vibration by converting electric energy into vibration energy.

In the present embodiment, the ultrasonic transducer 20 is a bolt-clamped Langevin-type transducer. The ultrasonic transducer 20 includes: piezoelectric elements that convert electric energy into vibration energy; and a vibration transmitting body 37 to which the piezoelectric elements 35 are attached. It suffices to dispose one or more piezoelectric elements 35. In the present embodiment, a plurality of piezoelectric elements 35 are arranged. In addition, the vibration transmitting body 37 is formed of a material having conductivity and high vibration transmissibility. The vibration transmitting body 37 is electrically insulated from the piezoelectric elements 35.

In a state in which the vibration generating device 5 is attached to the handle unit 4, a proximal end of the rod member 14 and a distal end of the vibration transmitting body 37 of the ultrasonic transducer 20 are connected to each other within the casing 11. An ultrasonic vibration can be thereby transmitted from the ultrasonic transducer 20 to the rod member 14. In addition, when the rotary operating knob 25 is rotated about the longitudinal axis C with respect to the casing 11, the ultrasonic transducer 20 and the generator unit 31 are rotated about the longitudinal axis C with respect to the casing 11 together with the rotary operating knob 25 and the shaft 12.

Figure 4:
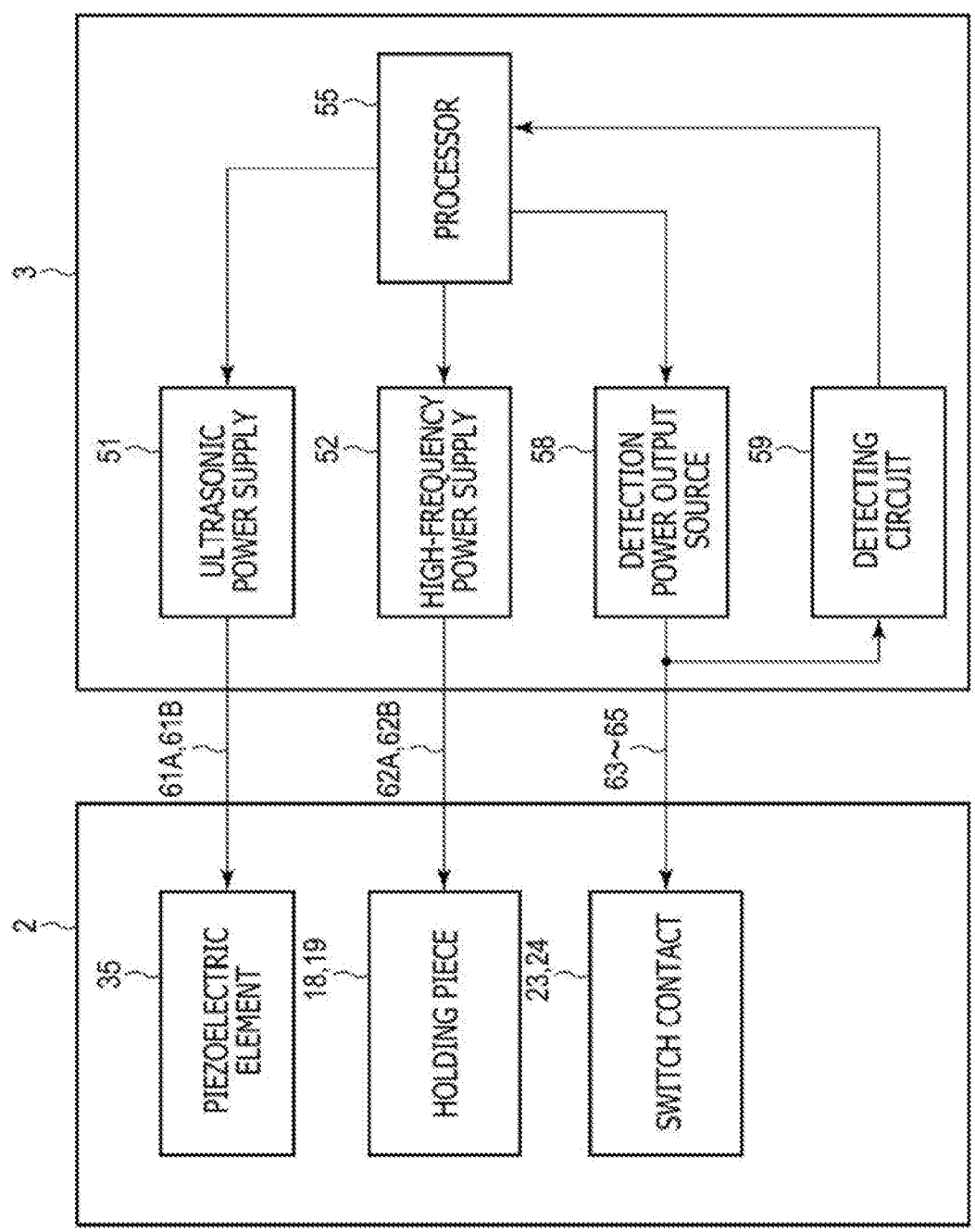
FIG. 4 is a block diagram schematically depicting a configuration that supplies electric energy from a power supply device to the treatment instrument according to the first embodiment.

As depicted in FIG. 4, the power supply device 3 includes an ultrasonic power supply 51, i.e., a first energy output source, as an output source outputting electric energy that actuates the treatment instrument 2. The ultrasonic power supply 51 is electrically connected to the piezoelectric elements 35 via electric paths 61A and 61B. The ultrasonic power supply 51 includes a waveform generator, a converting circuit, a transformer, and the like. The ultrasonic power supply 51 converts power from a battery power supply, an outlet power supply, or the like into alternating-current power of a certain frequency in a predetermined frequency range, for example. Then, the ultrasonic power supply 51 outputs the converted alternating-current power through the electric paths 61A and 61B. The ultrasonic power supply 51 thereby supplies the alternating-current power as electric energy that actuates the treatment instrument 2 to the piezoelectric elements 35 (ultrasonic transducer 20). The piezoelectric elements 35 convert the supplied electric energy into vibration energy. An ultrasonic vibration is thereby generated in the piezoelectric elements 35. In a state in which the vibration generating device 5 is attached to the handle unit 4, the ultrasonic vibration generated by the piezoelectric elements 35 is transmitted from the ultrasonic transducer 20 to the first holding piece 18 via the vibration transmitting body 37 and the rod member 14. Then, the transmitted ultrasonic vibration is applied as treatment energy to a treatment target held between the holding pieces 18 and 19. A processor 55 controls the supply of the alternating-current power, i.e., electric energy to the piezoelectric elements 35 by controlling the output from the ultrasonic power supply 51.

The power supply device 3 also includes a high-frequency power supply 52, i.e., a second energy output source, as an output source outputting electric energy that actuates the treatment instrument 2. In addition, at least a part of each of the first holding piece 18 and the second holding piece 19 is formed by a conductive material. The high-frequency power supply 52 is electrically connected to the first holding piece 18 via an electric path 62A, and is electrically connected to the second holding piece 19 via an electric path 62B. The high-frequency power supply 52 includes a waveform generator, a converting circuit, a transformer, and the like. The high-frequency power supply 52 converts power from a battery power supply, an outlet power supply, or the like into high-frequency power. Then, the high-frequency power supply 52 outputs the converted high-frequency power through the electric paths 61A and 61B. The high-frequency power supply 52 thus supplies the high-frequency power as electric energy that actuates the treatment instrument 2 to the first holding piece 18 and the second holding piece 19. The pair of holding pieces 18 and 19 thereby functions as electrodes having potentials different from each other. When the holding pieces 18 and 19 function as electrodes, a high frequency current flows through the treatment target between the holding pieces 18 and 19, and the high frequency current is applied as treatment energy to the treatment target. The processor 55 controls the supply of the high-frequency power, i.e., electric energy to the pair of holding pieces 18 and 19 by controlling the output from the high-frequency power supply 52.

Operating members 21 and 22 are attached to the casing 11. An operation of supplying electric energy from the power supply device 3 to the treatment instrument 2 is input at the operating members 21 and 22. In addition, switch contacts 23 and 24 are arranged within the casing 11. The switch contact 23 is electrically connected to a detection power output source 58 disposed in the power supply device 3 via electric paths 63 and 65. In addition, the switch contact 24 is electrically connected to the detection power output source 58 via electric paths 64 and 65. The detection power output source 58 includes a converting circuit, a transformer, and the like. The detection power output source 58 converts power from a battery power supply, an outlet power supply, or the like into direct-current power or alternating-current power. Then, the detection power output source 58 can output the converted direct-current power or the converted alternating-current power through the electric paths 63, 64, and 65. In a state in which an operation is input at the operating member 21, an electric conduction between the electric paths 63 and 65 is established at the switch contact 23. Therefore, in the state in which the operation is input at the operating member 21, electric energy is output from the detection power output source 58 through the electric paths 63 and 65, and thereby a current flows between the electric paths 63 and 65 at the switch contact 23. Therefore, whether or not a current flows between the electric paths 63 and 65 and/or the amplitude of the current flowing between the electric paths 63 and 65 or the like changes according to the operating input at the operating member 21. That is, the current flowing between the electric paths 63 and 65 changes based on the operating input at the operating member 21.

In addition, in a state in which an operation is input at the operating member 22, an electric conduction between the electric paths 64 and 65 is established at the switch contact 24. Therefore, in the state in which the operation is input at the operating member 22, electric energy is output from the detection power output source 58 through the electric paths 64 and 65, and thereby a current flows between the electric paths 64 and 65 at the switch contact 24. Therefore, whether or not a current flows between the electric paths 64 and 65 and/or the amplitude of the current flowing between the electric paths 64 and 65 or the like changes according to the operating input at the operating member 22. That is, the current flowing between the electric paths 64 and 65 changes based on the operating input at the operating member 22. Incidentally, the electric path 65 is a common line shared as a ground line for the switch contacts 23 and 24.

The power supply device 3 also includes a detecting circuit 59. The detecting circuit 59 detects, in at least one of the electric paths 63, 64, and 65, information regarding the current flowing through the electric path. For example, the detecting circuit 59 detects whether or not a current flows through each of the electric paths 63 and 64 or the current value of a current flowing through the electric path 65. The processor 55 obtains a result of the detection of the detecting circuit 59. Based on the obtained detection result, the processor 55 determines whether or not an operating input is performed at the operating member 21 or the operating member 22. Then, based on a result of the determination, the processor 55 controls the output of electric energy from the power supplies 51 and 52 to the treatment instrument 2.

When an operation is input at one of the operating members 21 and 22 in a state in which the treatment target is held between the holding pieces 18 and 19, electric energy is supplied from the power supply device 3 to the treatment instrument 2, and treatment energy is applied to the treatment target held between the holding pieces 18 and 19.

When an operation is input at the operating member 21, electric energy is supplied from the high-frequency power supply 52 to the treatment instrument 2, for example. Then, in a state in which the treatment target is held between the holding pieces 18 and 19, only a high frequency current is applied to the treatment target because electric energy is supplied from the high-frequency power supply 52 to the treatment instrument 2. A treatment that seals or coagulates the treatment target is thereby performed.

In addition, when an operation is input at the operating member 22, electric energy is supplied to the treatment instrument from both the ultrasonic power supply 51 and the high-frequency power supply 52, for example. Then, in a state in which the treatment target is held between the holding pieces 18 and 19, both the high frequency current and the ultrasonic vibration are applied to the treatment target at the same time because electric energy is supplied from both the ultrasonic power supply 51 and the high-frequency power supply 52 to the treatment instrument 2. A treatment that incises the treatment target at the same time as sealing or coagulating the treatment target is thereby performed.

Incidentally, while the two operating members (21 and 22) are arranged in the present embodiment, the number of operating members may be one, or may be three or more.

Figure 5:
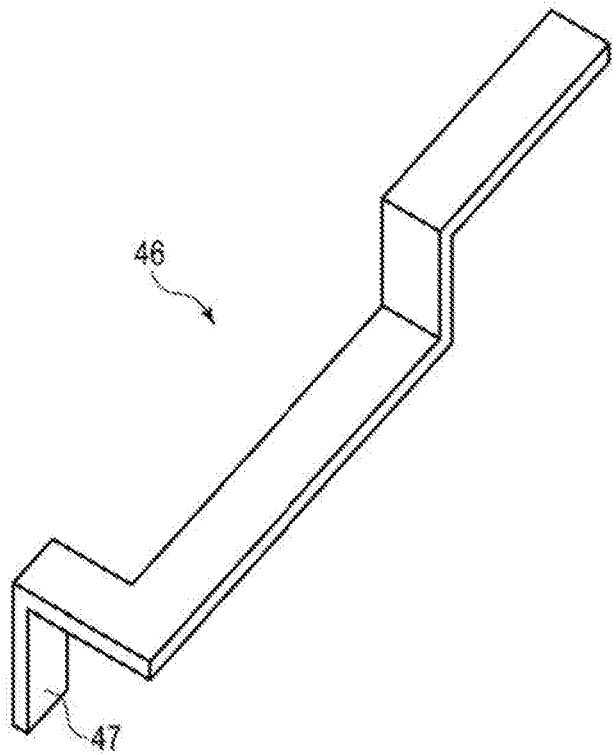
FIG. 5 is a perspective view schematically depicting a conductive member disposed in the coupler according to the first embodiment and forming a part of an electric path that supplies electric energy to a casing of the treatment instrument.

As depicted in FIG. 3 and FIG. 5, conductive members 46, i.e., signal transmitting members, having conductivity are disposed within the connector 42 of the coupler 41. In the present embodiment, four conductive members 46 (46A, 46B, 46C, and 46D) are arranged within the coupler 41. The conductive members 46 are electrically insulated from each other. Each of the conductive members 46 is extended from the cable connecting portion 43 to the distal end side. Each of the conductive members 46 forms one of the electric paths 62B, 63, 64, and 65 described hereinbefore.

One end of each of the conductive members 46 (46A, 46B, 46C, and 46D) is electrically connected, in the cable connecting portion 43, to one end of electric wiring 8 (8A, 8B, 8C, and 8D) extended within the cable 7. Here, one end of the electric wiring 8A is electrically connected to the conductive member 46A, and another end of the electric wiring 8A is electrically connected to the high-frequency power supply 52 of the power supply device 3. Thus, the conductive member 46A is electrically connected to the high-frequency power supply 52 via the electric wiring 8A extended within the cable 7. In addition, each of the conductive members 46B, 46C, and 46D is connected with one end of corresponding electric wiring (one of 8B, 8C, and 8D), and another end of each of the electric wiring 8B, 8C, and 8D is electrically connected to the detection power output source 58 of the power supply device 3. Thus, each of the conductive members 46B, 46C, and 46D is electrically connected to the detection power output source 58 via the electric wiring (one of 8B, 8C, and 8D) extended within the cable 7.

Another end of each of the conductive members 46 at a distal end portion of the connector 42 projects from the external surface of the connector 42. A projecting portion of each of the conductive members 46 which projecting portion projects from the external surface of the connector 42 forms a connection terminal 47 (47A, 47B, 47C, and 47D).

Figure 6:
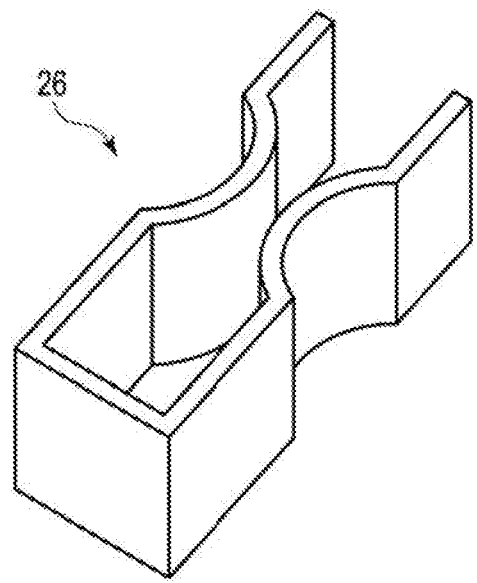
FIG. 6 is a perspective view schematically depicting a conductive member disposed in the casing of the treatment instrument according to the first embodiment.

As depicted in FIG. 2 and FIG. 6, conductive members 26, i.e., signal transmitting members, having conductivity are disposed within the casing 11. The conductive members 26 form an electric contact. In the present embodiment, four conductive members 26 (26A, 26B, 26C, and 26D), i.e., contacts within the handle, are arranged within the casing 11.

Here, the conductive member 26A is electrically connected to the movable shaft via electric wiring 28A extended within the casing 11. The movable shaft 15 is electrically connected to the second holding piece 19. Therefore, the conductive member 26A is electrically connected to the second holding piece 19 via the electric wiring 28A and the movable shaft 15. In addition, each of the conductive members 26B, 26C, and 26D is electrically connected to at least one of the operating members 21 and 22 via electric wiring (corresponding one of 28B to 28D) extended within the casing 11.

In a state in which the vibration generating device 5 is attached to the handle unit 4, each of the connection terminals 47 (47A, 47B, 47C, and 47D) engages with corresponding one of the conductive members 26 (one of 26A, 26B, 26C, and 26D) within the casing 11. Each of the connection terminals 47 and the corresponding conductive member 26 are electrically connected to each other by the engagement of each of the connection terminals 47 with the corresponding conductive member 26.

Here, the conductive member 46A and the conductive member 26A are electrically connected to each other between the vibration generating device 5 and the handle unit 4 by the engagement of the connection terminal 47A with the conductive member 26A. Thus, an electric connection is established from the second holding piece 19 to the high-frequency power supply 52 via the movable shaft 15, the electric wiring 28A, the conductive member 26A, the conductive member 46A, and the electric wiring 8A. That is, the electric path 62B is formed by the movable shaft 15, the electric wiring 28A, the conductive member 26A, the conductive member 46A, and the electric wiring 8A, and an electric connection is established between the conductive member disposed in the second holding piece 19 and the high-frequency power supply 52 via the electric path 62B.

In addition, the conductive member 46B and the conductive member 26B are electrically connected to each other between the vibration generating device 5 and the handle unit 4 by the engagement of the connection terminal 47B with the conductive member 26B. Thus, an electric connection is established from the switch contact 23 to the detection power output source 58 via the electric wiring 28B, the conductive member 26B, the conductive member 46B, and the electric wiring 8B. That is, the electric path 63 is formed by the electric wiring 28B, the conductive member 26B, the conductive member 46B, and the electric wiring 8B, and an electric connection is established between the switch contact 23 and the detection power output source 58 via the electric path 63.

Similarly, the connection terminal 47C and the conductive member 26C are engaged with each other. Thus, the electric path 64 is formed by the electric wiring 28C, the conductive member 26C, the conductive member 46C, and the electric wiring 8C, and an electric connection is established between the switch contact 24 and the detection power output source 58 via the electric path 64. In addition, the connection terminal 47D and the conductive member 26D are engaged with each other. Thus, the electric path 65 is formed by the electric wiring 28D, the conductive member 26D, the conductive member 46D, and the electric wiring 8D, and an electric connection is established between the switch contacts 23 and 24 and the detection power output source 58 via the electric path 65. Then, when the switch contacts 23 and 24 are electrically connected to the detection power output source 58 via the electric paths 63 to 65, the detecting circuit 59 becomes able to detect currents flowing through the electric paths 63 to 65, and the processor 55 becomes able to detect electric conduction at the switch contacts 23 and 24.

Figure 7:
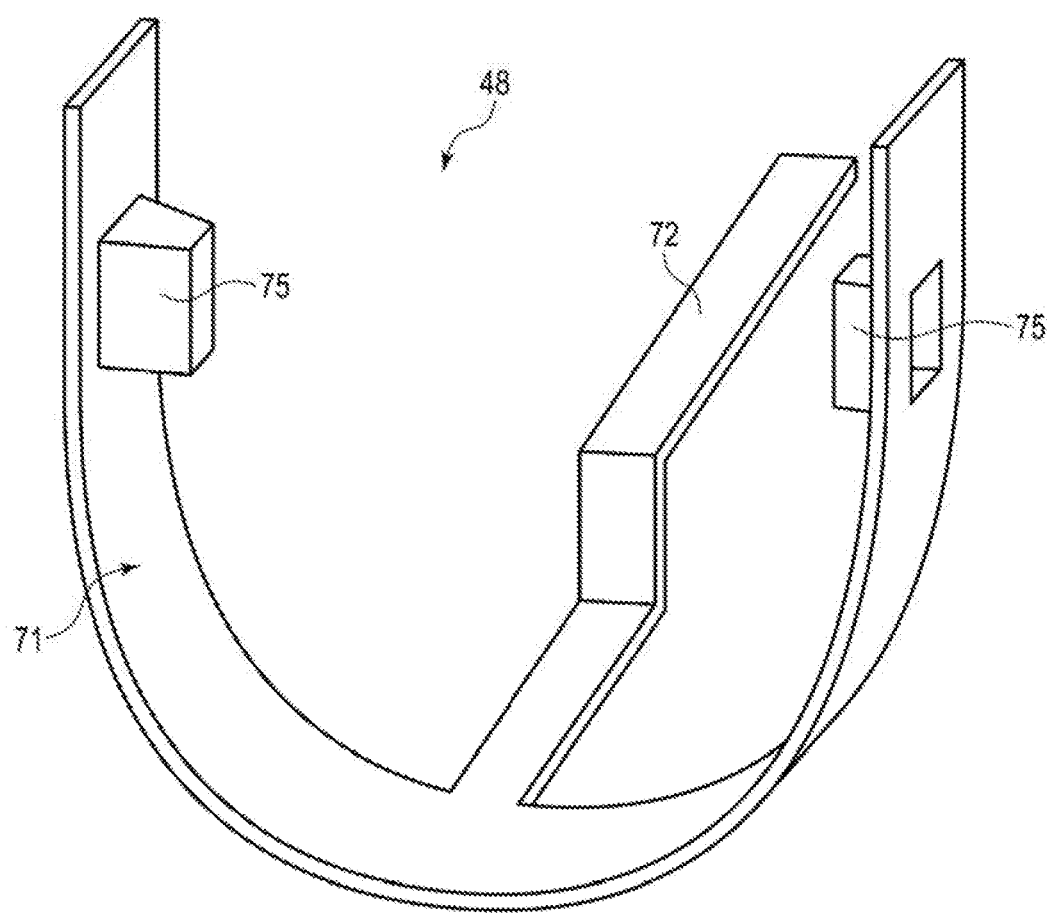
FIG. 7 is a perspective view schematically depicting a conductive member disposed in the coupler according to the first embodiment and forming a part of an electric path that supplies electric energy to the generator.

As depicted in FIG. 3 and FIG. 7, a conductive member 48 having conductivity is disposed within the connector 42 of the coupler 41. The conductive member 48 is electrically insulated from the conductive members 46. The conductive member 48 includes a U-shaped portion 71, i.e., a U-shaped electrode, disposed at a distal end portion of the conductive member 48 and an extended portion 72 extended from the U-shaped portion 71 to the proximal end side. A proximal end of the extended portion 72 is connected, in the cable connecting portion 43, to electric wiring 9 extended within the cable 7. The U-shaped portion 71 is formed in a U-shape, and is disposed in a state of opening in a direction intersecting (substantially perpendicular to) the longitudinal axis C. The U-shaped portion 71 forms a part of the inner circumferential surface of the groove portion 44 in a distal end portion of the groove portion 44 of the connector 42.

A protruding portion 75, i.e., a second electric contact, which protrudes inward, is disposed on the inner circumferential surface of the U-shaped portion 71. The protruding portion 75 protrudes inward from the inner circumferential surface of the groove portion 44. In the present embodiment, the U-shaped portion 71 has two protruding portions 75 arranged on opposite sides from each other with the longitudinal axis C interposed therebetween.

In the present embodiment, three conductive members 48 (48A, 48B, and 48C) are arranged within the connector 42. The conductive members 48 are electrically insulated from each other. Here, each of the conductive members 48A and 48B is electrically connected to the ultrasonic power supply 51 via corresponding electric wiring 9 (one of 9A and 9B). In addition, the conductive member 48C is electrically connected to the high-frequency power supply 52 via electric wiring 9C.

In addition, the widths of the U-shaped portions 71 (71A, 71B, and 71C) of the conductive members 48 (48A, 48B, and 48C) are different from each other. Hence, distances between the protruding portions 75 in the respective conductive members 48 are different from each other.

In the present embodiment, the U-shaped portion 71B is disposed on the proximal end side of the U-shaped portion 71A, and the U-shaped portion 71C is disposed on the proximal end side of the U-shaped portion 71B. In addition, the U-shaped portion 71B has a smaller width than the U-shaped portion 71A, and the U-shaped portion 71C has a smaller width than the U-shaped portion 71B. In the groove portion 44 of the connector 42, the width of the U-shaped portions 71 arranged therein is decreased from the distal end side toward the proximal end side.

As depicted in FIG. 2 and FIG. 3, an electric contact 34, i.e., a first electric contact, is disposed on a distal end portion of the housing 32 of the generator unit 31. The electric contact 34 is exposed to the outside of the housing 32. The electric contact 34 is formed in a ring shape having the longitudinal axis C as a center thereof, and is formed over the entire outer circumferential surface of the housing 32 about the longitudinal axis C.

Three electric contacts 34 (34A, 34B, and 34C) are formed on the outer circumferential surface of the housing 32. The electric contacts 34 are electrically insulated from each other. Here, each of the electric contacts 34A and 34B is electrically connected to the piezoelectric elements 35 of the ultrasonic transducer 20 via electric wiring 39A and 39B disposed within the housing 32. In addition, the electric contact 34C is electrically connected to the vibration transmitting body 37 of the ultrasonic transducer 20 via electric wiring 39C disposed within the housing 32.

In the present embodiment, the electric contact 34B is disposed on the proximal end side of the electric contact 34A, and the electric contact 34C is disposed on the proximal end side of the electric contact 34B. In addition, the diameter of the electric contact 34B is smaller than the diameter of the electric contact 34A, and the diameter of the electric contact 34C is smaller than the diameter of the electric contact 34B. Hence, the diameter of the disposed electric contacts 34 is decreased toward the proximal end side from the distal end side.

In a state in which the generator unit 31 is attached to the coupler 41, the housing 32 of the generator unit 31 is inserted in the groove portion 44 of the coupler 41. At this time, on the outside of each of the electric contacts 34 (34A, 34B, and 34C) of the generator unit 31, the corresponding conductive member 48 (one of 48A, 48B, and 48C) of the coupler 41 is disposed, and each of the electric contacts 34 is in contact with the protruding portions 75 of the corresponding conductive member 48. When each of the electric contacts 34 is in contact with the corresponding conductive member 48, an electric conduction between the electric contact 34 and the corresponding conductive member 48 is established between the generator unit 31 and the coupler 41.

Here, when the electric contact 34A and the conductive member 48A come into contact with each other, the electric contact 34A and the conductive member 48A are electrically connected to each other between the generator unit 31 and the coupler 41. Thus, an electric connection is established from the piezoelectric elements 35 to the ultrasonic power supply 51 via the electric wiring 39A, the electric contact 34A, the conductive member 48A, and the electric wiring 9A. That is, the electric path 61A is formed by the electric wiring 39A, the electric contact 34A, the conductive member 48A, and the electric wiring 9A, and an electric connection is established between the piezoelectric elements 35 and the ultrasonic power supply 51 via the electric path 61A.

Similarly, when the electric contact 34B and the conductive member 48B come into contact with each other, the electric path 61B is formed by the electric wiring 39B, the electric contact 34B, the conductive member 48B, and the electric wiring 9B, and an electric connection is established between the piezoelectric elements 35 and the ultrasonic power supply 51 via the electric path 61B. Then, when the electric connection between the piezoelectric elements 35 and the ultrasonic power supply 51 is established by the electric paths 61A and 61B, it becomes possible to supply electric energy from the ultrasonic power supply 51 to the ultrasonic transducer 20. Hence, the conductive members 48A and 48B form a part of power supply paths (61A and 61B) through which electric energy to be supplied to the ultrasonic transducer 20 of the generator unit 31 is transmitted.

In addition, when the electric contact 34C and the conductive member 48C come into contact with each other, the electric contact 34C and the conductive member 48C are electrically connected to each other between the generator unit 31 and the coupler 41. Thus, an electric connection is established from the first holding piece 18 to the high-frequency power supply 52 via the rod member 14, the vibration transmitting body 37, the electric wiring 39C, the electric contact 34C, the conductive member 48C, and the electric wiring 9C. That is, the electric path 62A is formed by the rod member 14, the vibration transmitting body 37, the electric wiring 39C, the electric contact 34C, the conductive member 48C, and the electric wiring 9C, and an electric connection is established between the first holding piece 18 and the high-frequency power supply 52 via the electric path 62A. Then, when the electric connection is established between the holding pieces 18 and 19 and the high-frequency power supply 52 by the electric paths 62A and 62B, it becomes possible to supply electric energy from the high-frequency power supply 52 to the holding pieces 18 and 19. Hence, the conductive member 46C and the conductive member 48C form a part of power supply paths (62A and 62B) through which electric energy to be supplied to the holding pieces 18 and 19 through a part of the ultrasonic transducer 20 of the generator unit 31 is transmitted.

In the present embodiment, the width of each of the U-shaped portions 71 (71A, 71B, and 71C) is formed to be a dimension corresponding to the diameter of the corresponding electric contact 34 (one of 34A, 34B, and 34C). In addition, the diameters of the electric contacts 34 are different from each other. Therefore, engagement of an electric contact (for example, 34A) with a conductive member (for example, 48B) other than the corresponding conductive member (for example, 48A) is prevented.

When the rotary operating knob 25 is rotated about the longitudinal axis C with respect to the casing 11, the generator unit 31 is rotated about the longitudinal axis C together with the shaft 12 and the end effector 13. Therefore, each of the electric contacts 34 is rotated about the longitudinal axis C with respect to the protruding portions 75 of the corresponding conductive member 48 by rotating the rotary operating knob 25. Here, each of the electric contacts 34 is formed over the entire circumference about the longitudinal axis C. Contact between the protruding portions 75 and the electric contact 34 is therefore maintained even when the generator unit 31 is rotated about the longitudinal axis C with respect to the casing 11. An electric connection between the generator unit 31 and the coupler 41 is therefore maintained even when the generator unit 31 is rotated with respect to the coupler 41.

Incidentally, the electric contacts 34 may not be formed over the entire circumference about the longitudinal axis C. It suffices for the electric contacts 34 to be formed over a range corresponding to a rotation range (movable range) of the end effector 13 about the longitudinal axis C.

The action and effect of the present embodiment will next be described. When a treatment is to be performed by using the treatment system 1, an operator connects the cable 7 to the power supply device 3, and attaches the vibration generating device 5 to the handle unit 4. At this time, each of the connection terminals 47, i.e., a third electric contact, and the corresponding conductive member 26, i.e., a fourth electric contact, engage with each other, and thereby an electric connection is established between each of the connection terminals 47 and the corresponding conductive member 26.

Then, the end effector 13 is inserted into a body cavity such as an abdominal cavity or the like, and a biological tissue such as a blood vessel or the like is disposed as a treatment target between the holding pieces 18 and 19. Then, the treatment target is held between the holding pieces 18 and 19 by an operation of the handle 17. When an operating input is performed by one of the operating members 21 and 22 in this state, at least one of a high frequency current and an ultrasonic vibration is applied as treatment energy to the treatment target held between the holding pieces 18 and 19.

In the present embodiment, the vibration generating device 5 is detachable from the handle unit 4 having the end effector 13 inserted into the body cavity. Therefore, after the treatment is performed by using the treatment instrument 2, the handle unit 4 is discarded, whereas the vibration generating device 5 can be reused after being cleaned and sterilized. In addition, in a casing where the generator unit 31 and the coupler 41 are configured to be able to be detachable from each other, each of the generator unit 31 and the coupler 41 can be cleaned and sterilized separately.

In the present embodiment, as described hereinbefore, each of the electric contacts 34 is formed over the entire circumference about the longitudinal axis C. Therefore, even when the generator unit 31 is rotated about the longitudinal axis C with respect to the casing 11 and the coupler 41, contact between the protruding portions 75 and the electric contacts 34 is maintained, and thus an electric connection between the generator unit 31 and the coupler 41 is maintained.

In addition, the coupler 41 is fixed to the casing 11, and is attached to so as to be rotatable about the longitudinal axis C with respect to the generator unit 31. Hence, even when the end effector 13 and the generator unit 31 are rotated about the longitudinal axis C with respect to the casing 11, the coupler 41 does not rotate with respect to the casing 11. Therefore, even when the end effector 13 and the generator unit 31 are rotated about the longitudinal axis C with respect to the casing 11, the cable 7 connected to the coupler 41 does not rotate with respect to the casing 11. Thus, the cable 7 is surely prevented from being twisted by rotating the end effector 13 about the longitudinal axis C.

In addition, in a state in which the vibration generating device 5 is attached to the handle unit 4, the generator unit 31 is housed within the coupler 41, and is not exposed to the outside of the treatment instrument 2. Therefore, during the usage of the treatment instrument 2, only the coupler 41 fixed to the casing 11 in the vibration generating device 5 is exposed to the outside. Therefore, even when an unintended external force acts on the coupler 41 in the external surface of the treatment instrument 2 in the treatment, the coupler 41 does not rotate with respect to the casing 11. Therefore, even when an unintended external force acts on the coupler 41, the external force is not transmitted to the generator unit 31. The end effector 13 is thus prevented from being rotated together with the generator unit 31 by the unintended external force acting on the external surface of the vibration generating device 5. Safety of the treatment is improved by preventing the end effector 13 from being rotated by the unintended external force acting on the external surface of the vibration generating device 5.

Second Embodiment

A second embodiment of the disclosed technology will be described with reference to FIG. 8. The second embodiment is obtained by modifying the configuration of the first embodiment as follows. Incidentally, the same parts as in the first embodiment are identified by the same numeral references, and description thereof will be omitted.

As depicted in FIG. 8, the connector 42 of the coupler 41 according to the present embodiment has a protruding portion 81 protruding to the distal end side, and the housing 32 of the generator unit 31 has a groove portion 82 with which the protruding portion 81 of the connector 42 can engage. The protruding portion 81 is extended along the longitudinal axis C, and is formed in substantially a shape cylindrical about the longitudinal axis C.

The groove portion 82 is recessed toward the distal end side in the proximal end portion of the housing 32. In the present embodiment, the protruding portion 81 of the coupler 41 engages with the groove portion 82 of the generator unit 31. The generator unit 31 is thereby attached to the coupler 41, and thus the vibration generating device 5 is formed. In addition, in a state in which the vibration generating device 5 is attached to the handle unit 4, only the coupler 41 in the vibration generating device 5 is exposed to the outside, and the generator unit 31 is housed within the casing 11.

Connection terminals 85 (85A, 85B, and 85C), i.e., first electric contacts, are arranged in the inner circumferential surface of the groove portion 82 of the generator unit 31 in place of the electric contacts 34 (34A, 34B, and 34C) according to the first embodiment. Each of the connection terminals 85 is electrically connected to corresponding electric wiring 39 (one of 39A, 39B, and 39C). Each of the connection terminals 85 is formed over the entire inner circumferential surface of the groove portion 82 about the longitudinal axis C.

Conductive members 83 (83A, 83B, and 83C) are arranged within the connector 42 of the coupler 41 in place of the conductive members 48 (48A, 48B, and 48C) according to the first embodiment. The proximal end of each of the conductive members 83 (83A, 83B, and 83C) is electrically connected, in the cable connecting portion 43, to corresponding electric wiring 9 (one of 9A, 9B, and 9C). The distal end of each of the conductive members 83 (83A, 83B, and 83C) protrudes outward in a radial direction from the outer circumferential surface of the protruding portion 81. Connection terminals 84 (84A, 84B, and 84C), i.e., second electric contacts, are formed by a protruding part of each of the conductive members 83 (83A, 83B, and 83C) which part protrudes from the outer circumferential surface of the protruding portion 81.

In a state in which the protruding portion 81 of the generator unit 31 engages with the groove portion 82 of the coupler 41, each of the connection terminals 85 (85A, 85B, and 85C) and the corresponding connection terminal 84 (one of 84A, 84B, and 84C) are in contact with each other. Each of the connection terminals 85 and the corresponding connection terminal 84 are thereby electrically connected to each other. Then, as in the first embodiment, the electric paths 61A and 61B are formed, and electric energy is supplied from the power supply device 3 to the generator unit 31 via the electric paths 61A and 61B. In addition, as in the first embodiment, the electric path 62A is formed, and electric energy is supplied from the power supply device 3 to the holding pieces 18 and 19 through a part of the generator unit 31 via the electric path 62A.

In the present embodiment, the connection terminals 85A, 85B, and 85C are formed over the entire circumference about the longitudinal axis C. Thus, even when the generator unit 31 is rotated about the longitudinal axis C with respect to the coupler 41, contact between the connection terminals 85A, 85B, and 85C and the corresponding connection terminals 84A, 84B, and 84C is maintained. Thus, also in the present embodiment, even when the generator unit 31 is rotated with respect to the coupler 41, electric connection between the generator unit 31 and the coupler 41 is maintained.

Common Configuration of Embodiments and the Like

A vibration generating device 5 is a vibration generating device 5 used in conjunction with a surgical device 4 having a holdable handle 16, 17, the vibration generating device 5 including: a housing 32, a generator 31 including a transducer 20 disposed within the housing 32, the transducer 20 generating vibration by being supplied with electric energy, and a first electric contact 34, 85 disposed on the housing 32; a connector 42 detachable from the handle 16, 17 and rotatable about a predetermined rotational axis with respect to the housing 32 of the generator 31; and a coupler 41 disposed in the connector 42, and having a second electric contact 75, 84 rotatable about the predetermined rotational axis with respect to the first electric contact 34 in a state in which an electric connection of the second electric contact 75, 84 to the first electric contact 34 is maintained.

It is to be noted that the disclosed technology of the present application is not limited to the foregoing embodiments, but can be modified variously without departing from the spirit of the invention in an implementation stage. In addition, the embodiments may be combined with each other and carried out as appropriate wherever possible, and effects of the combinations are obtained in that casing. Further, the foregoing embodiments include inventions in various stages, and various inventions can be extracted by appropriate combinations in a plurality of disclosed constituent elements.

In sum, one aspect of the disclosed technology is directed to a treatment instrument having a vibration generating device and a handle for operation. The vibration generating device comprises a housing and a generator including a transducer disposed within the housing. The transducer generates vibration by using electric energy and a first electric contact disposed on the housing. A connector is rotatable about a predetermined rotational axis with respect to the housing of the generator. A coupler is disposed in the connector and having a second electric contact rotatable about the predetermined rotational axis with respect to the first electric contact in a state in which an electric connection of the second electric contact to the first electric contact is maintained. The connector further includes a conductive member forming a part of an electric path of a current that flows based on an operating input at an operating member provided on the handle.

In the treatment instrument of vibration generating device, the connector includes a third electric contact disposed on an external surface of the connector and an electric connection is established between the operating member of the handle and the electric path by electrically connecting the third electric contact to a fourth electric contact disposed in the handle. The connector includes a socket disposed on an outside of the housing of the generator. The second electric contact is disposed on an inner circumferential surface of the socket and the third electric contact is disposed on an outer circumferential surface of the socket. The second electric contact includes a first U-shaped electrode and a second U-shaped electrode having a smaller width than the first U-shaped electrode and the first U-shaped electrode is located on a distal end side with respect to the second U-shaped electrode. The connector includes a conductive member electrically connected to the second electric contact and forming a part of a power supply path through which the electric energy to be supplied to the generator is transmitted. The treatment instrument of vibration generating device further comprises a cable extending from the connector and having the electric path and the power supply path extended within the cable. The connector includes an attachment to be engaged with the handle and the connector is attached to the handle by engaging the attachment with the handle. The connector has a protruding portion protruding to a distal end side. The housing of the generator includes a groove portion with which the protruding portion engages. The first electric contact is disposed on an inner circumferential surface of the groove portion and the second electric contact is disposed on an outer circumferential surface of the protruding portion.

Another aspect of the disclosed technology is directed to a treatment instrument comprises a handle unit having a handle for operation. A rod member is supported by the handle and transmitting vibration on a longitudinal axis. A treatment unit is disposed at a distal end of the rod member and performing treatment by applying the vibration to a biological tissue. A vibration generating device is configured to be attached to the handle unit. The vibration generating device includes a housing and a generator including a transducer disposed within the housing. The transducer generates vibration by using electric energy and a first electric contact disposed on the housing. A connector rotatable about a predetermined rotational axis with respect to the housing of the generator. A coupler is disposed in the connector and having a second electric contact rotatable about the predetermined rotational axis with respect to the first electric contact in a state in which an electric connection of the second electric contact to the first electric contact is maintained. The connector further includes a conductive member forming a part of an electric path of a current that flows based on an operating input at an operating member provided on the handle.

A further aspect of the disclosed technology is directed to a treatment system comprises a treatment instrument including a handle unit. The handle unit includes a handle for operation. A rod member is supported by the handle and transmitting vibration on a longitudinal axis. A treatment unit is disposed at a distal end of the rod member and performing treatment by applying the vibration to both a biological tissue and a vibration generating device. A cable having one end connected to the vibration generating device and a power supply device connected to an opposed end of the one end of the cable. The vibration generating device includes a housing and a generator including a transducer disposed within the housing. The transducer generates the vibration by using electric energy and a first electric contact is disposed on the housing. The connector rotatable about a predetermined rotational axis with respect to the housing of the generator. A coupler is disposed in the connector and having a second electric contact rotatable about the predetermined rotational axis with respect to the first electric contact in a state of being electrically connected to the first electric contact. The connector further includes a conductive member connected to the power supply device and the cable and forming a part of an electric path of a current that flows based on an operating input at an operating member provided on the handle.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A treatment instrument having a vibration generating device and a handle for operation, the vibration generating device comprising:
    a housing;
    a generator including a transducer disposed within the housing, the transducer generates vibration by using electric energy and a first electric contact disposed on the housing;
    a connector rotatable about a predetermined rotational axis with respect to the housing of the generator; and
    a coupler disposed in the connector and having a second electric contact rotatable about the predetermined rotational axis with respect to the first electric contact in a state in which an electric connection of the second electric contact to the first electric contact is maintained, wherein
    the connector further includes
        a conductive member forming a part of an electric path of a current that flows based on an operating input at an operating member provided on the handle, and
        a protruding portion protruding to a distal end side,
    the housing of the generator includes a groove portion with which the protruding portion engages,
    the first electric contact is disposed on an inner circumferential surface of the groove portion, and
    the second electric contact is disposed on an outer circumferential surface of the protruding portion.

2. The treatment instrument of claim 1, wherein
    the connector includes a third electric contact disposed on an external surface of the connector, and
    an electric connection is established between the operating member of the handle and the electric path by electrically connecting the third electric contact to a fourth electric contact disposed in the handle.

3. The treatment instrument of claim 1, wherein
    the connector includes a conductive member electrically connected to the second electric contact and forming a part of a power supply path through which the electric energy to be supplied to the generator is transmitted.

4. The treatment instrument of claim 3, further comprising
    a cable extending from the connector and having the electric path and the power supply path extended within the cable.

5. The treatment instrument of claim 1, wherein the connector includes an attachment to be engaged with the handle, and the connector is attached to the handle by engaging the attachment with the handle.

6. The treatment instrument of claim 1, wherein the coupler and the generator are each disposed on a same longitudinal axis.

7. A treatment instrument comprising:
    a handle unit having a handle for operation;
    a rod member supported by the handle and transmitting vibration on a longitudinal axis;
    a treatment unit disposed at a distal end of the rod member and performing treatment by applying the vibration to a biological tissue; and
    a vibration generating device configured to be attached to the handle unit,
    the vibration generating device includes
        a housing,
        a generator including a transducer disposed within the housing, the transducer generates vibration by using electric energy and a first electric contact disposed on the housing,
        a connector rotatable about a predetermined rotational axis with respect to the housing of the generator, and
        a coupler disposed in the connector, and having a second electric contact rotatable about the predetermined rotational axis with respect to the first electric contact in a state in which an electric connection of the second electric contact to the first electric contact is maintained,
    the connector further includes
        a conductive member forming a part of an electric path of a current that flows based on an operating input at an operating member provided on the handle, and a protruding portion protruding to a distal end side, the housing of the generator includes a groove portion with which the protruding portion engages, the first electric contact is disposed on an inner circumferential surface of the groove portion, and the second electric contact is disposed on an outer circumferential surface of the protruding portion.

8. The treatment instrument of claim 7, wherein the connector is detachably attachable to the handle unit.

9. A treatment system comprising:

a treatment instrument including a handle unit, the handle unit includes a handle for operation, a rod member supported by the handle and transmitting vibration on a longitudinal axis, a treatment unit disposed at a distal end of the rod member and performing treatment by applying the vibration to both a biological tissue and a vibration generating device;

a cable having one end connected to the vibration generating device; and a power supply device connected to an opposed end of the one end of the cable, wherein the vibration generating device includes a housing, a generator including a transducer disposed within the housing, the transducer generates the vibration by using electric energy, and a first electric contact disposed on the housing, a connector rotatable about a predetermined rotational axis with respect to the housing of the generator, and a coupler disposed in the connector, and having a second electric contact rotatable about the predetermined rotational axis with respect to the first electric contact in a state of being electrically connected to the first electric contact, the connector further includes a conductive member connected to the power supply device and the cable, and forming a part of an electric path of a current that flows based on an operating input at an operating member provided on the handle, and a protruding portion protruding to a distal end side, the housing of the generator includes a groove portion with which the protruding portion engages, the first electric contact is disposed on an inner circumferential surface of the groove portion, and the second electric contact is disposed on an outer circumferential surface of the protruding portion.

10. The treatment system of claim 9, wherein the connector is detachably attachable to the handle unit.

\* \* \* \* \*